United States Patent
Kasumi et al.

(10) Patent No.: US 9,661,081 B2
(45) Date of Patent: May 23, 2017

(54) WIRELESS IMAGE TRANSFER SYSTEM AND WIRELESS IMAGE TRANSFER METHOD

(71) Applicant: OLYMPUS CORPORATION, Tokyo (JP)

(72) Inventors: Makoto Kasumi, Hachioji (JP); Hideki Tashiro, Hino (JP); Junichi Tashiro, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/140,834

(22) Filed: Apr. 28, 2016

(65) Prior Publication Data

US 2016/0241647 A1 Aug. 18, 2016

Related U.S. Application Data

(63) Continuation of application No. PCT/JP2014/078109, filed on Oct. 22, 2014.

(30) Foreign Application Priority Data

Feb. 10, 2014 (JP) ................. 2014-023552

(51) Int. Cl.
*G06F 15/167* (2006.01)
*H04L 29/08* (2006.01)
(Continued)

(52) U.S. Cl.
CPC .......... *H04L 67/12* (2013.01); *A61B 1/00016* (2013.01); *G06T 7/0002* (2013.01);
(Continued)

(58) Field of Classification Search
CPC .... A61B 1/00016; G06T 7/0002; H04N 7/18; H04N 7/183; H04L 67/1095; H04L 43/08
(Continued)

(56) References Cited

U.S. PATENT DOCUMENTS 6,987,881 B2 * 1/2006 Nakajima ............... G06T 5/008
382/173
2001/0055061 A1 12/2001 Onishi et al.
(Continued)

FOREIGN PATENT DOCUMENTS

JP 2001-275950 A 10/2001
JP 2001-353124 A 12/2001
(Continued)

OTHER PUBLICATIONS

Jan. 27, 2015 Search Report issued in International Patent Application No. PCT/JP2014/078109.
(Continued)

*Primary Examiner* — Tauqir Hussain
(74) *Attorney, Agent, or Firm* — Oliff PLC

(57) ABSTRACT

A wireless image transfer system includes an image quality judgement unit configured to judge reception states of a first image transmitted in a first frequency band by a first image wireless block and a second image transmitted in a second frequency band by a second image wireless block and image qualities of the received images; and a second control unit configured to sort the reception states into a good state, a bad state, and an intermediate state, select a first image signal in the good state, steadily operate the second image wireless block and periodically operate the first image wireless block in the bad state, and select an image with a better quality from the first image signal and a second image signal and output the selected image in the intermediate state.

8 Claims, 5 Drawing Sheets

(51) Int. Cl.
- *H04N 7/18* (2006.01)
- *A61B 1/00* (2006.01)
- *G06T 7/00* (2017.01)
- *H04L 12/26* (2006.01)

(52) U.S. Cl.
CPC .......... *H04L 43/08* (2013.01); *H04L 67/1095* (2013.01); *H04N 7/18* (2013.01); *H04N 7/183* (2013.01)

(58) Field of Classification Search
USPC ....................................................... 709/217
See application file for complete search history.

(56) References Cited

U.S. PATENT DOCUMENTS

| | | | |
|---|---|---|---|
| 2004/0082834 A1 | 4/2004 | Onishi et al. | |
| 2004/0085441 A1 | 5/2004 | Onishi et al. | |
| 2006/0200323 A1* | 9/2006 | Hayakawa | G02B 27/0012 703/2 |
| 2009/0016601 A1* | 1/2009 | Kunugi | G06T 11/001 382/162 |
| 2009/0187376 A1* | 7/2009 | Ogiwara | G06F 19/24 702/158 |
| 2009/0213241 A1* | 8/2009 | Fukuei | G06K 9/00248 348/222.1 |
| 2010/0213386 A1* | 8/2010 | Man | G01N 1/32 250/400 |
| 2011/0320595 A1* | 12/2011 | Konishi | G06F 19/3412 709/224 |
| 2012/0134556 A1* | 5/2012 | Kono | G06T 7/0012 382/128 |
| 2013/0265402 A1* | 10/2013 | Tashiro | A61B 1/00016 348/74 |
| 2013/0282003 A1* | 10/2013 | Messerly | A61B 17/320068 606/37 |
| 2014/0002627 A1* | 1/2014 | Tashiro | A61B 8/12 348/71 |
| 2015/0279061 A1* | 10/2015 | Kutsuna | G06T 11/003 382/131 |
| 2016/0261846 A1* | 9/2016 | Kasumi | H04N 7/18 |

FOREIGN PATENT DOCUMENTS

| | | |
|---|---|---|
| JP | 2012-186701 A | 9/2012 |
| JP | 2014-022999 A | 2/2014 |

OTHER PUBLICATIONS

Nov. 4, 2015 Office Action issued in Japanese Patent Application No. 2015-537480.

* cited by examiner

WIRELESS IMAGE TRANSFER SYSTEM AND WIRELESS IMAGE TRANSFER METHOD

CROSS REFERENCE TO RELATED APPLICATION

This application is a continuation application of PCT/JP2014/078109 filed on Oct. 22, 2014 and claims benefit of Japanese Application No. 2014-023552 filed in Japan on Feb. 10, 2014, the entire contents of which are incorporated herein by this reference.

BACKGROUND OF INVENTION

1. Field of the Invention

The present invention relates to a wireless image transfer system and a wireless image transfer method for transferring a medical image.

2. Description of the Related Art

In recent years, a medical observation apparatus, such as an endoscope and a surgical microscope, configured to observe an operation region in a medical action, such as a surgery, is widely used. A surgery using the medical observation apparatus is also frequently performed, such as an endoscopic surgery in which an endoscope is inserted into a body cavity like an abdominal cavity or a thoracic cavity, from a small fistula opened on a body surface of a patient, and an organ in the body cavity is treated under the endoscopic observation. An example of an advantage of the endoscopic surgery includes reduced invasion to the patient.

The surgical image observation apparatus includes an image pickup device, and the image pickup device allows picking up an observed image in the body cavity of the patient. The observed image obtained by picking up the image can be outputted to a monitor or recorded, and people involved in the surgery, such as an operator, an assistant, and a nurse, can share the image.

A medical image from the medical observation apparatus can be supplied to a plurality of monitors in an operating room. The operator can observe the medical image through a monitor that is easy to view according to a standing position. In consideration of a degree of freedom of the installation of the monitors, wireless transfer is recently utilized in some cases for the transfer of the medical image from the medical observation apparatus to the monitors. For example, to reduce influence of interference, wireless transfer with a communication band of a 60 GHz band that is not generally used is adopted for medical use in some cases.

However, an antenna with a high directivity is generally adopted in a wireless device that uses a radio wave of the 60 GHz band, and a straightness of the radio wave is also strong. Therefore, receiver sensitivity may be degraded, and forward data may be missed, depending on the standing position of the operator, a direction of the monitor, an obstacle of transfer existing in the operating room, movement of a person, and the like.

In regard to the deterioration of reception, a transmission and reception apparatus is disclosed in Japanese Patent Application Laid-Open Publication No. 2012-186701 (hereinafter, called Literature 1), wherein communication with a communication band of a 60 GHz band and communication with a communication band of a 5 GHz band are adopted, a communication band to be preferentially used is set, and which one of the communication bands is to be selected can be switched according to a reception state.

SUMMARY OF THE INVENTION

An aspect of the present invention provides a wireless image transfer system including a transmitter and a receiver, the transmitter including: a first image wireless block configured to wirelessly transfer an image signal in a first frequency band; a second image wireless block configured to wirelessly transfer the image signal in a second frequency band different from the first frequency band; and a first control unit configured to control the first and second image wireless blocks, and the receiver including: a third image wireless block configured to receive a signal transmitted by the first image wireless block to obtain a first image signal; a fourth image wireless block configured to receive a signal transmitted by the second image wireless block to obtain a second image signal; a reception state acquisition unit configured to acquire information of a reception state in the third image wireless block; an image quality judgement unit configured to judge image qualities of images based on the first and second image signals obtained by the third and fourth image wireless blocks, respectively; and a second control unit configured to sort the reception state in the third image wireless block into a good state, a bad state, and an intermediate state based on the information of the reception state, select the first image signal from the third image wireless block in the good state, steadily operate the second image wireless block and periodically operate the first image wireless block in the bad state, and select an image with a better quality from the first and second image signals and output the selected image in the intermediate state.

An aspect of the present invention provides a wireless image transfer method in a wireless image transfer system capable of image transfer between a transmitter and a receiver using first and second frequency bands, the wireless image transfer method including: detecting, in the receiver, whether a reception state of the image transfer in the first frequency band is a good state, a bad state, or an intermediate state that is a state between the good state and the bad state; acquiring an image by performing the image transfer using the first frequency band if the detected reception state is the good state; periodically performing the image transfer of the first frequency band while acquiring an image by performing the image transfer of the second frequency band if the detected reception state is the bad state; and performing the image transfer using both of the first and second frequency bands and judging an image quality of each image transferred in the first and second frequency bands to acquire an image with a better quality if the detected reception state is the intermediate state.

DETAILED DESCRIPTION OF THE PREFERRED EMBODIMENT(S)

Hereinafter, an embodiment of the present invention will be described in detail with reference to the drawings.

Figure 1:
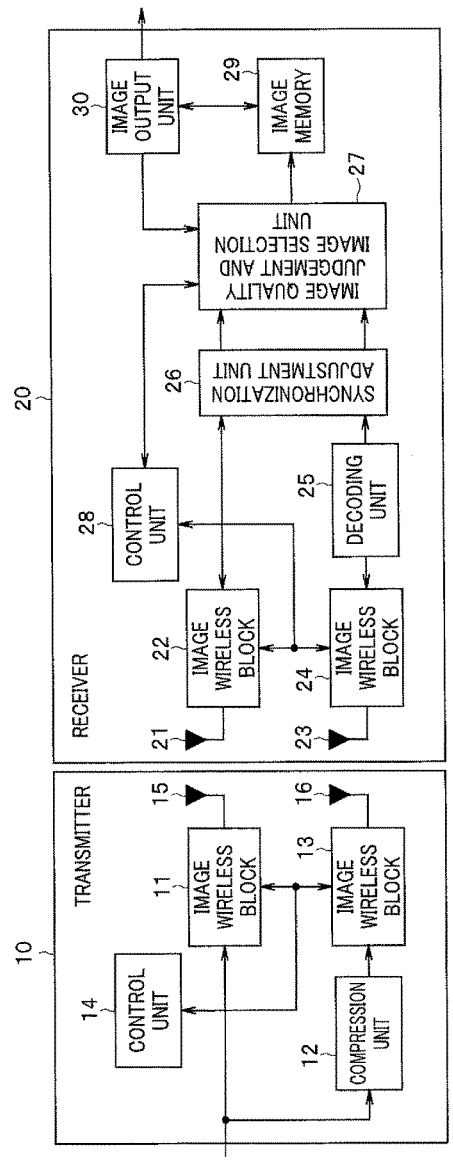
FIG. 1 is a block diagram showing a wireless image transfer system according to an embodiment of the present invention.
Figure 2:
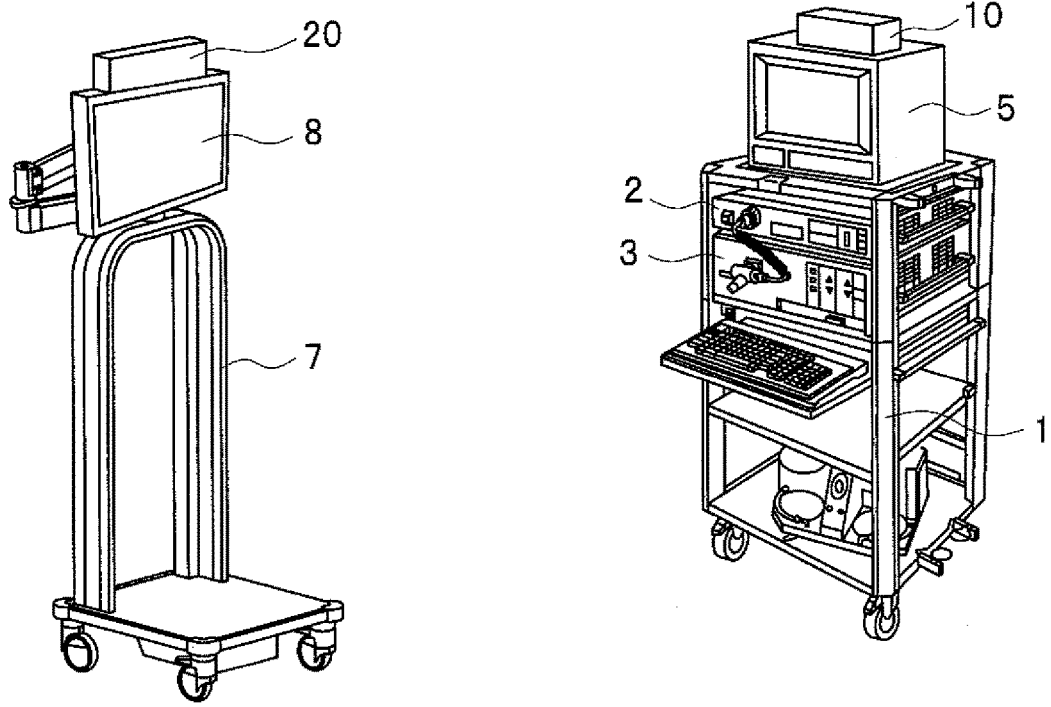
FIG. 2 is an explanatory view showing arrangement of a transmitter and a receiver included in the wireless image transfer system of FIG. 1.

FIG. 1 is a block diagram showing a wireless image transfer system according to an embodiment of the present invention. FIG. 2 is an explanatory view showing arrangement of a transmitter and a receiver included in the wireless image transfer system of FIG. 1.

In FIG. 2, two carts 1 and 7 are arranged in, for example, an operating room not shown. A processor 2 configured to process an image from an observation apparatus such as an endoscope not shown, a light source apparatus 3 configured to supply light to the endoscope, a monitor 5, and the like are mounted on the cart 1 of the carts 1 and 7. The processor 2 is configured to be connected to the observation apparatus through a cable not shown and is configured to be able to process an image from the observation apparatus to supply an image signal to the monitor 5 through a cable not shown. As a result, an observed image from the observation apparatus is displayed on a display screen of the monitor 5. A transmitter 10 is further mounted above the monitor 5, and an image signal from the processor 2 is also provided to the transmitter 10 through a cable not shown.

On the other hand, a monitor 8 is attached to the cart 7. A receiver 20 is mounted above the monitor 8. The transmitter 10 and the receiver 20 can mutually perform wireless communication. The transmitter 10 transmits an image signal from the observation apparatus to the receiver 20 through a wireless transfer path not shown. The receiver 20 can receive the image from the transmitter 10 and output the image to the monitor 8. As a result, the observed image from the observation apparatus is displayed on a display screen of the monitor 8.

Note that although the image is transferred from the transmitter 10 to the receiver 20, the transmitter 10 and the receiver 20 can mutually transmit and receive various data. Although an example of transmission of the observed image from the observation apparatus is illustrated, the transmitter 10 and the receiver 20 can transfer various images.

In FIG. 1, an image signal from the processor 2 or the like is inputted to the transmitter 10. The image signal is provided to an image wireless block 11 and a compression unit 12. The compression unit 12 compresses the inputted image signal and outputs the image signal to an image wireless block 13. The image wireless blocks 11 and 13 are controlled by a control unit 14 to perform wireless transmission of the image signal.

In the present embodiment, the image wireless block 11 performs communication based on a first wireless communication system in a first frequency band, and the image wireless block 13 performs communication based on a second wireless communication system in a second frequency band. The first and second frequency bands are wireless frequency bands different from each other. The image wireless block 11 transmits the image signal through an antenna 15, and the image wireless block 13 transmits the image signal through an antenna 16.

Conventionally, an example of a wireless frequency band for performing communication includes a 5 GHz band defined by an IEEE (Institute of Electrical and Electronics Engineers) 802.11 ac standard. In the communication of the 5 GHz band, a theoretical maximum transfer speed is 3 Gbps or higher. In recent years, a frequency band is defined by an IEEE 802.11 ad standard, in which the theoretical maximum transfer speed is 6 Gbps or higher, and the frequency band used for communication is a 60 GHz band.

In the description of the present embodiment, for example, the wireless communication block 11 performs communication using the 60 GHz band as the first frequency band, and the wireless communication block 13 performs communication using the 5 GHz band as the second frequency band.

In the communication using the 60 GHz band, a data transfer speed can be easily increased, and an uncompressed HD (high definition) image can be transferred. On the other hand, straightness of a radio wave is strong, and the communication tends to be influenced by an obstacle. By contrast, the straightness of a radio wave is unlikely to be influenced by an obstacle in the communication of the 5 GHz band. On the other hand, it is difficult to increase the data transfer speed, and the communication is significantly influenced by an interference because the communication is used in various wireless devices.

Therefore, the communication based on the 60 GHz band is preferentially used as much as possible in the present embodiment, and the communication of the 5 GHz band is also utilized according to a judgement of a reception state and an image quality in the image transfer utilizing the communication of the 60 GHz band. Operation of the image wireless blocks 11 and 13 is controlled by the control unit 14.

Antennas 21 and 23 of the receiver 20 are configured to transmit and receive radio waves to and from the antennas 15 and 16, respectively. An image wireless block 22 receives the image signal transmitted by the image wireless block 11 from a high frequency signal induced in the antenna 21 and outputs the image signal to a synchronization adjustment unit 26. An image wireless block 24 receives the image signal transmitted by the image wireless block 13 from a high frequency signal induced in the antenna 23 and outputs the image signal to a decoding unit 25. The decoding unit 25 obtains the image signal before the compression based on a decoding process corresponding to the compression unit 12 of the transmitter 10 and outputs the image signal to the synchronization adjustment unit 26.

Figure 3:
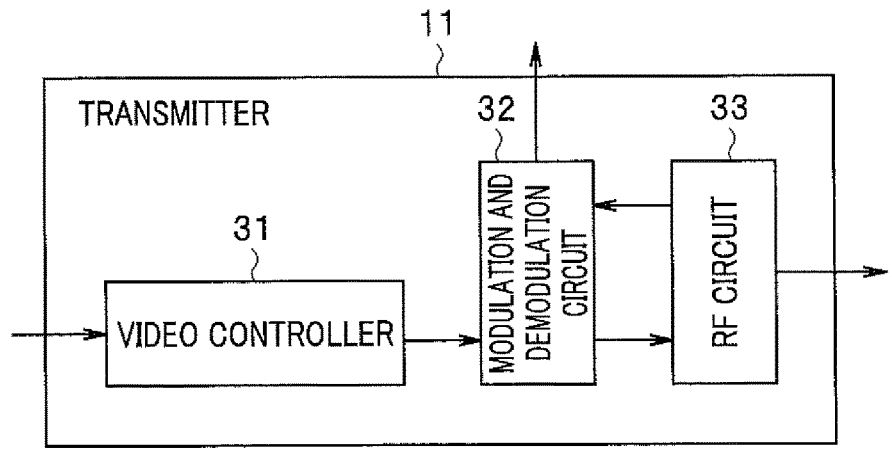
FIG. 3 is a block diagram showing an example of a specific configuration of an image wireless block 11 in FIG. 1.
Figure 4:
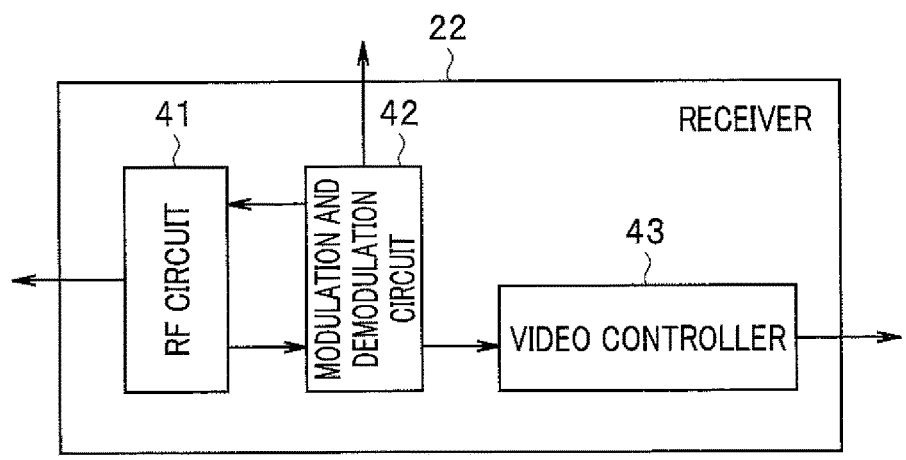
FIG. 4 is a block diagram showing an example of a specific configuration of an image wireless block 22 in FIG. 1.

FIGS. 3 and 4 are block diagrams showing examples of specific configurations of the image wireless blocks 11 and 22 in FIG. 1, respectively.

The transmitter 11 includes a video controller 31, a modulation and demodulation circuit 32, and an RF circuit 33. The video controller 31 provides, for example, an image signal supplied from the processor 2 to the modulation and demodulation circuit 32. The modulation and demodulation circuit 32 applies a predetermined modulation process to the inputted image signal and then outputs the image signal to the RF circuit 33. Note that the modulation and demodulation circuit 32 is configured to add an error correcting code to the image signal to be outputted in the modulation process. The RF circuit 33 converts the modulation signal to a high frequency signal and performs wireless transmission through the antenna 15.

The RF circuit 33 also receives a transmission signal from the image wireless block 22 of the receiver 20 through the antenna 15 and outputs the transmission signal to the modulation and demodulation circuit 32. The modulation and demodulation circuit 32 returns the received signal to a baseband. For example, when the receiver 20 transmits a command for controlling the transmitter 10, the modulation and demodulation circuit 32 is configured to obtain the command and output the command to the control unit 14. As described later, the control unit 14 can also control the image wireless blocks 11 and 13 according to the command from the receiver 20.

The receiver 22 includes an RF circuit 41, a modulation and demodulation circuit 42, and a video controller 43. The RF circuit 41 receives a transmission signal from the wireless communication block 11 of the transmitter 10 and outputs a reception signal to the modulation and demodulation circuit 42. The modulation and demodulation circuit 42 returns the received signal to a baseband to obtain an image signal transmitted from the transmitter 10 and outputs the image signal to the video controller 43. The video controller 43 is configured to output the inputted image signal to the synchronization adjustment unit 26 of a later stage.

In the present embodiment, the modulation and demodulation circuit 42 executes error correction processing using the error correcting code added at the transmission, in the course of the demodulation process. The modulation and demodulation circuit 42 can obtain an error rate from a result of the error correction processing and output the error rate to a control unit 28. The modulation and demodulation circuit 42 is also configured to acquire RSSI (received signal strength indication) information, such as information of receiver sensitivity, obtained in the course of the baseband processing and output the RSSI information to the control unit 28. In this way, the modulation and demodulation circuit 42 acquires information for judging the reception state in the communication of the 60 GHz band and outputs the information to the control unit 28.

In FIG. 1, the image signal (hereinafter, also called a first image signal) transferred by the wireless communication of the 60 GHz band from the image wireless block 22 is inputted to the synchronization adjustment unit 26, and an image signal (hereinafter, also called a second image signal) transferred by the wireless communication of the 5 GHz band from the decoding unit 25 is inputted to the synchronization adjustment unit 26. The synchronization adjustment unit 26 is controlled by the control unit 28 to adjust synchronization of the first and second image signals and output the first and second image signals to an image quality judgement and image selection unit 27.

The first and second image signals are inputted to the image quality judgement and image selection unit 27. In the present embodiment, both of the first and second image signals are inputted to the synchronization adjustment unit 26 and the image quality judgement and image selection unit 27 in some cases, and only one of the first and second image signals is inputted to the synchronization adjustment unit 26 and the image quality judgement and image selection unit 27 in other cases, as described later.

The image quality judgement and image selection unit 27 is controlled by the control unit 28 to judge the image quality of the images obtained by the first and second image signals and select the image signal with a higher quality to output the image signal to an image memory 29. For example, the image quality judgement and image selection unit 27 makes a judgement based on PSNR (peak signal-to-noise ratio) values.

The image quality judgement process and the image selection process of the image quality judgement and image selection unit 27 are controlled by the control unit 28. Based on the judgement result of the reception state in the wireless communication of the 60 GHz band, the control unit 28 outputs a control signal indicating whether to cause the image quality judgement and image selection unit 27 to execute the judgement process of the image quality and the image selection process. Depending on the judgement result of the reception state in the communication of the 60 HGz band, the control unit 28 is configured to cause the image quality judgement and image selection unit 27 to select one of the first and second image signals according to the judgement result of the reception state. The image quality judgement and image selection unit 27 outputs the selected image to the image memory 29.

In this way, the image quality judgement and image selection unit 27 judges the image quality of the first image signal of the baseband after decoding. The judgement of the reception state performed by the modulation and demodulation circuit 42 of the image wireless block 22 is obtained by the process for the signal before decoding, and the judgement can be made with a relatively small circuit scale. In the present embodiment, the image quality judgement by the image quality judgement and image selection unit 27 using the first image signal that is a baseband signal after decoding is used to a limited extent, and this allows efficient and sure image transfer without increasing the circuit scale.

The image quality judgement and image selection unit 27 outputs the result of the image selection to an image output unit 30. The image output unit 30 is configured to read the image selected by the image quality judgement and image selection unit 27 from the image memory 29 based on the judgement result of the image selection and to output the image to the monitor 8.

The control unit 28 generates a command to be transmitted to the transmitter 10 based on the information of the reception state from the image wireless block 22 and controls the image wireless block 22 to transmit the generated command to the transmitter 10.

In the present embodiment, the control unit 28 sets a mode for performing communication only in the 60 GHz band (hereinafter, called a normal mode), a mode for performing communication in both of the 60 GHz band and the 5 GHz band (hereinafter, called a selection mode), and a mode for periodically performing communication in the 60 GHz band while performing communication in the 5 GHz band (hereinafter, called a non-normal mode) based on the information of the reception state, and the control unit 28 transmits commands corresponding to the modes to the transmitter 10.

The image quality judgement and image selection unit 27 outputs an image based on wireless communication of the 60 GHz band in the normal mode, outputs an image based on wireless communication of the 5 GHz band in the non-normal mode, and outputs an image selected by executing the judgement process of the image quality and the image selection process in the selection mode.

Figure 5:
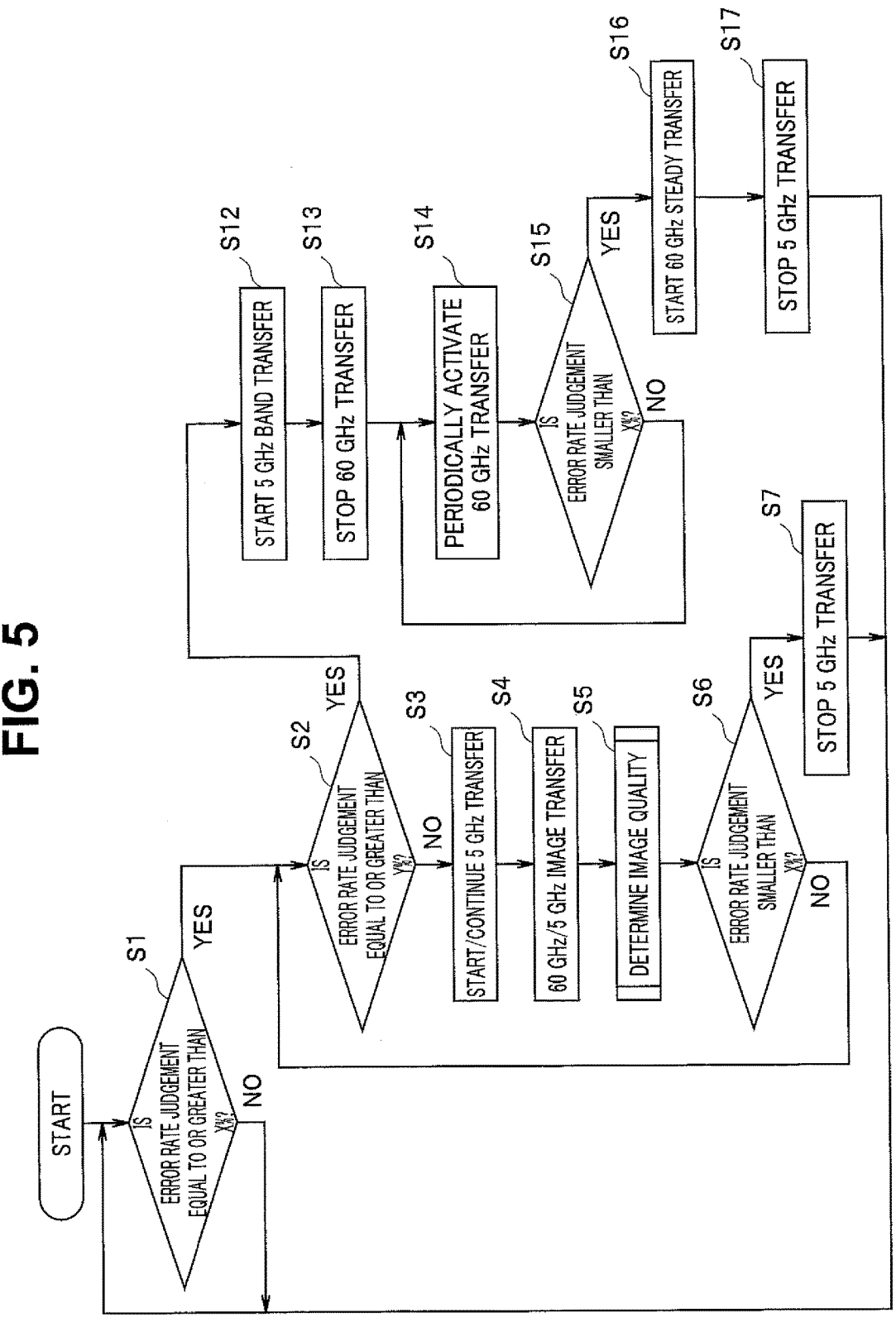
FIG. 5 is a flowchart showing wireless transfer control in the present embodiment.
Figure 6:
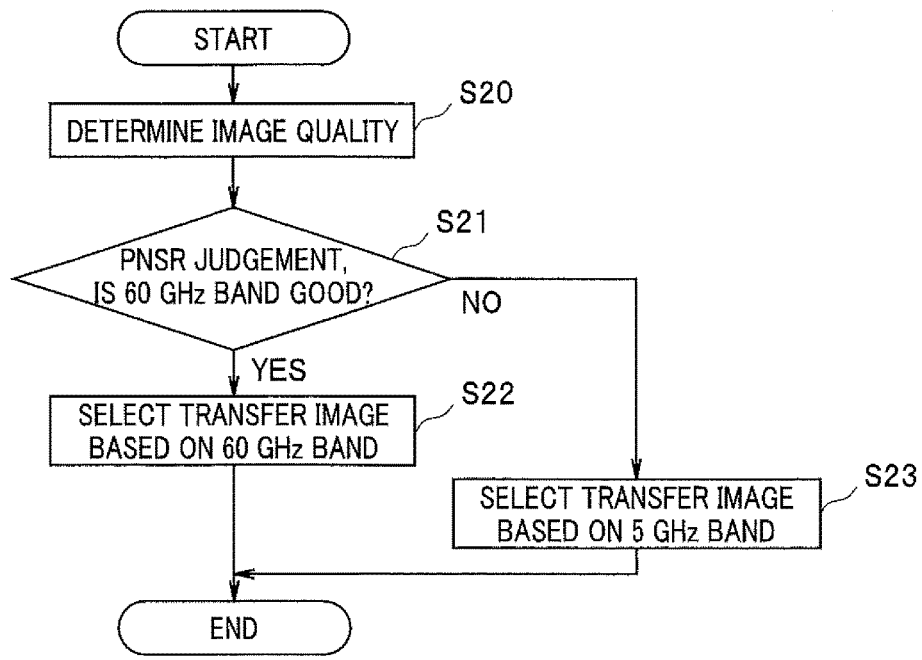
FIG. 6 is a flowchart showing wireless transfer control in the present embodiment.
Figure 7:
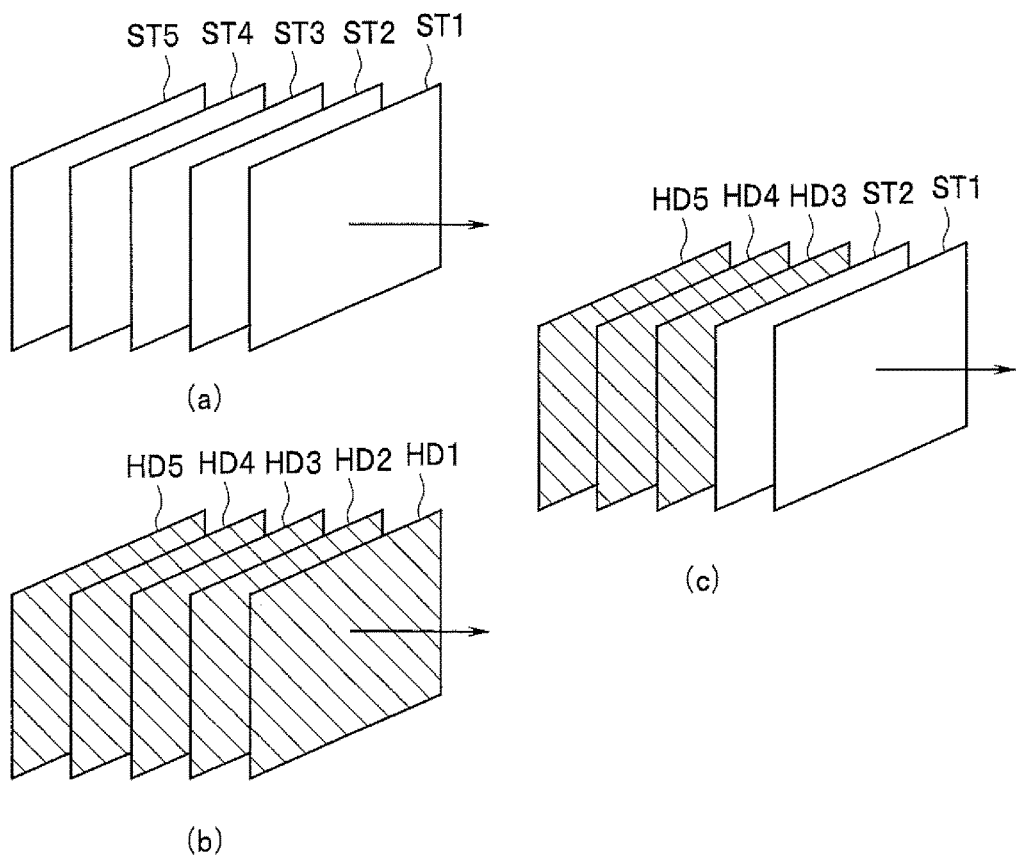
FIG. 7 is an explanatory view for describing selection of images.

Next, operation of the embodiment with the configuration will be described with reference to FIGS. 5 to 7. FIGS. 5 and 6 are flowcharts showing wireless transfer control in the present embodiment. FIG. 7 is an explanatory view for describing selection of an image.

Now, it is assumed that operation in the normal mode for performing communication in the 60 GHz band is performed. That is, the control unit 28 of the receiver 20 is generating a command for instructing transfer of an image to the transmitter 10 in the 60 GHz band. The command is transmitted from the image wireless block 22 through the antenna 21 and received by the image wireless block 11 through the antenna 15 of the receiver 20. The modulation and demodulation circuit 32 of the image wireless block 11 outputs the command from the receiver 20 to the control unit 14. The control unit 14 stops the operation of the image wireless block 13 according to the command and causes the image wireless block 11 to perform the image transfer of the 60 GHz band.

In the normal mode, the image wireless block 11 transmits the image signal of the observed image or the like in the 60 GHz band from the antenna 15. The image wireless block 22 of the receiver 20 receives the image signal through the antenna 21.

The modulation and demodulation circuit 42 of the image wireless block 22 demodulates the received image to obtain the image signal of the baseband. The image signal is supplied to the image quality judgement and image selection unit 27 through the synchronization adjustment unit 26. In the course of the demodulation, the image wireless block 22 acquires the information of the reception state, such as an error rate, an SN ratio, and RSSI, and outputs the information to the control unit 28.

The control unit 28 determines whether the reception state is good, bad, or an intermediate state between good and bad based on the information of the reception state from the image wireless block 22. For example, the control unit 28 judges whether the reception state is good based on a first threshold, judges whether the reception state is bad based on a second threshold, and judges whether the reception state is the intermediate state based on whether the state is between the first and second thresholds.

For example, the control unit 28 judges that the reception state is good based on whether the error rate is smaller than X % that is the first threshold. For example, the control unit 28 judges that the reception state is bad based on whether the error rate is equal to or greater than Y % that is the second threshold. For example, the control unit 28 judges that the reception state is the intermediate state based on whether the error rate is equal to or greater than X % and smaller than Y %.

In step S1 of FIG. 5, the control unit 28 judges whether the error rate is equal to or greater than X %, that is, whether the reception state is not good. If the error rate is smaller than X %, the control unit 28 judges that the reception state of the communication of 60 GHz is good and executes the same process as before to continue the communication of the 60 GHz band.

Here, it is assumed for example that a person in an operating room moves to a position between the transmitter 10 and the receiver 20, and the reception state in the communication of the 60 GHz band is deteriorated. When the error rate becomes equal to or greater than X %, the control unit 28 judges that the reception state is not good, and in step S2, the control unit 28 judges whether the error rate is equal to or greater than Y %, that is, whether the reception state is bad (step S2).

If the error rate in the communication of the 60 GHz band becomes equal to or greater than Y % due to the influence of an obstacle or the like, the control unit 28 judges that the reception state of the communication of 60 GHz is bad and makes a transition to the non-normal mode.

In the non-normal mode, the control unit 28 starts the communication of the 5 GHz band and generates a command for stopping the communication of the 60 GHz band. First, the command for starting the communication of the 5 GHz band is transmitted from the image wireless block 22 through the antenna 21 (step S12). The image wireless block 11 of the receiver 20 receives the command and supplies the command to the control unit 14. The control unit 14 starts the operation of the image wireless block 13 to start the communication of the 5 GHz band.

As a result, the image signal, such as the observed image, is compressed by the compression unit 12. The image signal is then supplied to the image wireless block 13 and transmitted from the antenna 16 in the 5 GHz band. Note that the image transfer in the 60 GHz band is continued until the image transfer in the 60 GHz band is surely switched to the image transfer in the 5 GHz band.

The image wireless block 24 of the receiver 20 receives the image signal through the antenna 23 and outputs the image signal of the baseband to the decoding unit 25. The decoding unit 25 decodes the image signal to obtain the original image signal and outputs the image signal to the image quality judgement and image selection unit 27 through the synchronization adjustment unit 26.

When the transition to the non-normal mode is instructed from the control unit 28, and the image signal based on the communication of the 5 GHz band is inputted, the image quality judgement and image selection unit 27 outputs the image signal based on the communication of the 5 GHz band to the image memory 29. The image quality judgement and image selection unit 27 notifies the control unit 28 of the output of the image of the 5 GHz band. As a result, the control unit 28 generates a command for stopping the image transfer of the 60 GHz band and transmits the command to the transmitter 10. When the control unit 14 of the transmitter 10 receives the command for stopping the communication of the 60 GHz band, the control unit 14 stops the operation of the image wireless block 11 (step S13).

Next, to return to the image transfer of the 60 GHz band, the control unit 28 periodically, at a predetermined cycle, generates commands for executing the image transfer in the 60 GHz band in order to check the reception state in the 60 GHz band and causes the image wireless block 22 to transmit the commands (step S14).

The control unit 14 of the transmitter 10 controls the image wireless block 11 according to the commands to periodically perform the image transfer in the 60 GHz band. Note that the image transfer is executed to check the reception state, and the image transfer for supplying the image signal to the monitor 8 is performed in the 5 GHz band.

In step S15, the control unit 28 judges whether the reception state in the communication of the 60 GHz band is good, or for example, judges whether the error rate is smaller than X %. If the control unit 28 judges that the reception state is not returned to the good state, the control unit 28 returns the process to step S14 to continue the non-normal mode for periodically performing the image transfer in the 60 GHz band to check the reception state, while performing the image transfer in the 5 GHz band.

Here, it is assumed that an obstacle between the transmitter 10 and the receiver 20 is removed, and the reception state of the image transfer is returned to the good state. In this case, the error rate becomes smaller than X % for example, and the control unit 28 moves the process to step S16 to generate a command for steadily continuing the communication of the 60 GHz band. The command starts the transfer of the image signal based on the 60 GHz band from the transmitter 10. The image wireless block 22 receives the signal of the 60 GHz band and outputs the signal to the image quality judgement and image selection unit 27 through the synchronization adjustment unit 26. The image quality judgement and image selection unit 27 is controlled by the control unit 28 to select the image signal based on the communication of the 60 GHz band and output the image signal to the image memory 29. When the control unit 28 detects that the image signal of the 60 GHz band is outputted to the image memory 29 based on a notification from the image quality judgement and image selection unit 27, the control unit 28 generates a command for stopping the image transfer of the 5 GHz band (step S17) and returns to the normal mode (step S1).

In the present embodiment, the return of the reception state to the intermediate state is not enough for the return from the non-normal mode to the normal mode, and the return from the non-normal mode to the normal mode is based on the condition that the reception state is good. This prevents frequent switches of the image transfer between the 60 GHz band and the 5 GHz band when, for example, the reception state changes around the second threshold. The stability of communication and the stability of image are ensured.

In the present embodiment, in the intermediate state in which the reception state is not bad, but is not surely good either, the selection mode is set to perform the image transfer in both of the 60 GHz band and the 5 GHz band. The images are judged, and the image with a better quality is selectively used.

Now, it is assumed that the reception state is changed from the good state to the intermediate state, or for example, the error rate becomes equal to or greater than X % and smaller than Y %. In this case, the control unit 28 judges that the reception state is changed to the intermediate state based on the information of the reception state from the image wireless block 22 and sets the selection mode for performing the image transfer in both of the 60 GHz band and the 5 GHz band. The control unit 28 generates a command for starting the image transfer of the 5 GHz band, in addition to the image transfer of the 60 GHz band that is already performed (step S3). The command is transmitted from the antenna 21 and received through the antenna 15 of the receiver 20.

The control unit 14 causes the image wireless block 13 to start the operation to transmit a compressed image signal in the 5 GHz band (step S4). The image signal is received by the image wireless block 24 of the receiver 20 and decoded by the decoding unit 25. The image signal is then supplied to the synchronization adjustment unit 26.

In the selection mode, the first image signal based on the communication of the 60 GHz band is provided from the image wireless block 22 to the synchronization adjustment unit 26, and the second image signal based on the communication of the 5 GHz band is provided from the decoding unit 25 to the synchronization adjustment unit 26. The synchronization adjustment unit 26 adjusts the synchronization of the first image transferred in the 60 GHz band and the second image transferred in the 5 GHz band to allow the image quality judgement and image selection unit 27 to judge the image quality of the first and second image signals of a same frame and to select an image. The image quality judgement and image selection unit 27 judges the image quality of the first image signal and the second image signal in step S5 based on, for example, PSNR.

FIG. 6 shows an image quality judgement process in step S5 of FIG. 5. In each frame, the image quality judgement and image selection unit 27 judges the image quality of the first image signal and the second image signal, frame by frame (step S20). The image quality judgement and image selection unit 27 judges which one of the images has a good quality in step S21. If the image quality of the frame based on the image transferred in the 60 GHz band is good, the image quality judgement and image selection unit 27 selects and outputs the first image signal in step S22. If the image quality of the frame based on the image transferred in the 5 GHz band is good, the image quality judgement and image selection unit 27 selects and outputs the second image signal in step S23.

FIG. 7 illustrates this. FIGS. 7(*a*) and 7(*b*) show images inputted to the image quality judgement and image selection unit 27, respectively, and FIG. 7(*c*) shows selected images. FIG. 7 shows five frames continuously transferred in rectangular frames, and arrows indicate a time direction. FIG. 7(*a*) illustrates frames ST1 to ST5 transferred in the 5 GHz band, and FIG. 7(*b*) illustrates frames HD1 to HD5 (oblique lines) transferred in the 60 GHz band. The frames ST1 to ST5 of FIG. 7(*a*) and the frames HD1 to HD5 of FIG. 7(*b*) are images of the same frames, respectively, synchronized by the synchronization adjustment unit 26.

The image quality is judged for each frame, and the image with a better quality is selected and outputted. In the example of FIG. 7(*c*), the frames ST1 and ST2 based on the second image signal in the communication of the 5 GHz band are selected for the first two frames, and the frames HD3 to HD5 based on the second image signal in the communication of the 60 GHz band are selected for the third to fifth frames.

The image quality judgement and image selection unit 27 outputs information of the selected frames to the image output unit 30. As a result, the image output unit 30 can surely read and output the selected images from the image memory 29, without missing or overlapping images.

In step S6, the control unit 28 checks the reception state in the 60 GHz band in order to return to the normal mode. The control unit 28 judges whether the reception state in the communication of the 60 GHz band is good, or for example, whether the error rate is smaller than X %. If the control unit 28 judges that the reception state is not good yet, the control unit 28 returns the process to step S2 to judge whether to continue the selection mode or to make a transition to the non-normal mode.

Here, it is assumed that an obstacle between the transmitter 10 and the receiver 20 is removed, and the reception state of the image transfer has returned to the good state. In this case, the error rate becomes smaller than X % for example, and the control unit 28 moves the process to step S7. The control unit 28 generates a command for stopping the image transfer of the 5 GHz band and returns to the normal mode.

In this way, the transfer of the first frequency band of the transfers of the first and second frequency bands is preferentially used in the present embodiment. The reception state is sorted into the good, bad, and intermediate states based on the information indicating the reception state, and the image transfer of the second frequency band is individually used only in the bad state. In the intermediate state, the image quality of the first and second image signals of the baseband is judged, and which one of the images transferred in the first and second frequency bands is to be used is determined according to the judgement result. That is, in the intermediate state in which the transfer in the 60 GHz band may not be always bad, the image transfer of the 60 GHz band is performed when the image quality is good, and the image transfer in the 5 GHz band is utilized depending on the image quality.

As a result, the transfer in the second frequency band is reduced, and the image transfer in the first frequency band capable of high-speed transfer of high-quality images is prioritized. In the intermediate state, the image transfer that allows obtaining high-quality images can be adopted from the image transfers in the first and second frequency bands. This allows efficient and sure image transfer without increasing the circuit scale.

Note that the 60 GHz band is adopted as the first frequency band, and 5 GHz is adopted as the second frequency band in the example described in the embodiment. However, the first and second frequency bands are not limited to these frequency bands, and it is obvious that various frequency bands can be adopted. Furthermore, a plurality of transfer channels are used in each frequency band, and for example, the image signal is transferred in one transfer channel. Different transfer channels can be designated as the first and second frequency bands in the present embodiment. For example, a predetermined transfer channel of the 60 GHz band may be set as the first frequency band, and another predetermined transfer channel of the 60 GHz band may be set as the second frequency band.

The present invention is not limited to each of the embodiments described above, and in an execution phase, the constituent elements can be modified without departing from the concept of the present invention to embody the present invention. Furthermore, various inventions can be formed based on appropriate combinations of a plurality of constituent elements disclosed in each of the embodiments. For example, some of the constituent elements in the all constituent elements illustrated in the embodiments may be deleted. Furthermore, constituent elements across different embodiments may also be appropriately combined.

Many of the controls and the functions mainly described in the flowcharts among the techniques described here can be set by a program, and a computer can read and execute the program to realize the controls and the functions. All or part of the program can be recorded or stored as a computer program product in a portable medium, such as a non-volatile memory like a flexible disk or a CD-ROM, or in a storage medium, such as a hard disk and a volatile memory. The program can be distributed or provided at the product shipment or through a portable medium or a communication line. The user can download the program through a communication network to install the program on a computer or can install the program on a computer from a recording medium to easily realize the present embodiment.

What is claimed is:

1. A wireless image transfer system comprising a transmitter and a receiver,
   the transmitter comprising:
   a first wireless device wirelessly transferring an image signal in a first frequency band;
   a second wireless device wirelessly transferring the image signal in a second frequency band different from the first frequency band; and
   a first controller controlling the first and second wireless devices, and
   the receiver comprising:
   a third wireless device receiving and demodulating a signal transmitted by the first wireless device to obtain a first image signal;
   a fourth wireless device receiving and demodulating a signal transmitted by the second wireless device to obtain a second image signal;
   a demodulation circuit provided in the third wireless device, the demodulation circuit acquiring, in a process of demodulating the signal transmitted by the second wireless device, information of an evaluation index indicating a reception state in the third wireless device;
   a second controller programmed to:
   receive the first and second image signals obtained by the third and fourth wireless devices, respectively;
   calculate the evaluation index regarding an image quality of the first image, and calculate the evaluation index regarding an image quality of the second image; and
   when sorting cases where the evaluation index indicating the reception state is smaller than a first threshold, is equal to or greater than a second threshold, and is equal to or greater than the first threshold and smaller than the second threshold, respectively, into good, bad and intermediate reception states of the third wireless device, select the first image signal from the third wireless device in the good state, steadily operate the second wireless device and periodically operate the first wireless device in the bad state, and select an image with a better quality of the first and second image signals based on the evaluation index regarding the image quality and output the selected image in the intermediate state.

2. The wireless image transfer system according to claim 1, wherein
   the second controller sends out a command to the first controller to operate only the first wireless device in the good state, operate the first and second wireless device in the intermediate state, and steadily operate the second wireless device and periodically operate the first wireless device in the bad state.

3. The wireless image transfer system according to claim 1, wherein
   the second controller is further programmed to:
   synchronize the first and second image signals from the third and fourth wireless devices.

4. The wireless image transfer system according to claim 3, wherein for each frame, the second controller selects the first and second image signals outputted by the synchronization adjustment unit according to the evaluation index regarding the image quality in the intermediate state.

5. The wireless image transfer system according to claim 1, wherein
   the first frequency band is a frequency band higher than the second frequency band.

6. A wireless image transfer method in a wireless image transfer system capable of image transfer between a transmitter and a receiver using first and second frequency bands, the wireless image transfer method comprising:
   obtaining, in the receiver, an evaluation index indicating a reception state of the image transfer in a first frequency band, and detecting whether the reception state of the image transfer in the first frequency band is a good state, a bad state, or an intermediate state that is a state between the good state and the bad state, respectively, depending on whether the evaluation index is smaller than a first threshold, is equal to or greater than a second threshold, or is equal to or greater than the first threshold and smaller than the second threshold;
   acquiring an image by performing the image transfer using the first frequency band if the detected reception state is the good state;
   periodically performing the image transfer of the first frequency band while acquiring an image by performing the image transfer of the second frequency band if the detected reception state is the bad state; and performing the image transfer using both of the first and second frequency bands and, calculating an evaluation index regarding an image quality of each image transferred in the first and second frequency bands, and judging an image with a better image quality to acquire the image with a better quality if the detected reception state is the intermediate state.

7. The wireless image transfer method according to claim 6, wherein
the evaluation index indicating the reception state is an error rate.

8. The wireless image transfer method according to claim 6, wherein
the evaluation index regarding the image quality is a peak signal-to-noise ratio.

* * * * *